(12) United States Patent
Sung et al.

(10) Patent No.: US 11,608,490 B2
(45) Date of Patent: Mar. 21, 2023

(54) COMPOSITION FOR ENHANCING HAIR GROWTH-INDUCING ABILITY OF ADIPOSE STEM CELLS COMPRISING UDENAFIL AS ACTIVE INGREDIENT

(71) Applicant: INDUSTRY-ACADEMIC COOPERATION FOUNDATION, YONSEI UNIVERSITY, Seoul (KR)

(72) Inventors: Jong Hyuk Sung, Seongnam-si (KR); Na Hyun Choi, Incheon (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 762 days.

(21) Appl. No.: 16/427,084

(22) Filed: May 30, 2019

(65) Prior Publication Data
US 2019/0367879 A1    Dec. 5, 2019

(30) Foreign Application Priority Data
May 30, 2018    (KR) .......................... 10-2018-0062118

(51) Int. Cl.
| | | |
|---|---|---|
| *C12N 5/0775* | (2010.01) | |
| *A61K 35/28* | (2015.01) | |
| *A61K 38/20* | (2006.01) | |
| *A61P 17/14* | (2006.01) | |

(52) U.S. Cl.
CPC ............ *C12N 5/0667* (2013.01); *A61K 35/28* (2013.01); *A61K 38/208* (2013.01); *A61K 38/2026* (2013.01); *A61P 17/14* (2018.01); *C12N 2501/01* (2013.01)

(58) Field of Classification Search
None
See application file for complete search history.

(56) References Cited

U.S. PATENT DOCUMENTS

2009/0304654 A1*   12/2009   Lue ..................... C12N 5/0676
                                                          435/377

FOREIGN PATENT DOCUMENTS

| CN | 102307561 | 1/2012 |
|---|---|---|
| KR | 10-1686229 | 12/2016 |

OTHER PUBLICATIONS

Blaber et al. "Analysis of in vitro secretion profiles from adipose-derived cell populations." Journal of Translational Medicine 10.1 (2012): 1-16. (Year: 2012).*
Hoke et al. "Preconditioning by phosphodiesterase-5 inhibition improves therapeutic efficacy of adipose-derived stem cells following myocardial infarction in mice." Stem Cells 30.2 (2012): 326-335. (Year: 2012).*
Kim et al. "Safety, tolerability and pharmacokinetics of udenafil, a novel PDE-5 inhibitor, in healthy young Korean subjects." British journal of clinical pharmacology 65.6 (2008): 848-854. (Year: 2008).*
Kim et al., "The Molecular Mechanism Underlying the Proliferating and Preconditioning Effect of Vitamin C on Adipose-Derived Stem Cells" *Stem Cells and Development*, 2014, 23(12):1364-1376.
Won et al., "Letter to the Editor: Hair growth promoting effects of adipose tissue-derived stem cells" *Journal of Dermatological Science*, 2010, 57:134-137.
Choi et al., "Minoxidil Promotes Hair Growth through Stimulation of Growth Factor Release from Adipose-Derived Stem Cells" *Int. J. Mal. Sci.* 2018, 19(691), 15 pages.
Hun Jeong et al., "Combined Therapeutic Effect of Udenafil and Adipose-derived Stem Cell (ADSC)/Brain-derived Neurotrophic Factor (BDNF)eMembrane System in a Rat Model of Cavernous Nerve Injury" Urology 2013, 81(5), 1108.e7-1108.e14.
*Neovascular eye disease*, edited by Yisheng Zhong et al., People's Military Medical Press, 1st edition, Sep. 2006, pp. 153-155 (English Abstract provided).
Office Action issued in Corresponding Chinese Application No. 201910458212.7, dated Apr. 26, 2022 (English translation provided).

* cited by examiner

*Primary Examiner* — Emily A Cordas
(74) *Attorney, Agent, or Firm* — Norton Rose Fulbright US LLP (57) ABSTRACT

The present invention relates to a hair growth-inducing ability enhancing effect of adipose stem cells obtained by performing treatment with udenafil and performing culture, and provides a composition for preventing or treating alopecia, or promoting hair growth, comprising, as an active ingredient, adipose stem cells obtained by performing treatment with udenafil and performing culture, IL-4, or IL-12B. In a case where a culture medium of adipose stem cells is treated with udenafil and cultured, IL-4 and IL-12B expression levels are increased in the adipose stem cells, and thus maturation of hair follicle cells is further promoted, so that hair growth can be induced. In addition, in a case where IL-4 and IL-12B, which are expressed in the adipose stem cells obtained by performing treatment with udenafil and performing culture, are applied to skin tissue, hair growth can be induced.

7 Claims, 10 Drawing Sheets

COMPOSITION FOR ENHANCING HAIR GROWTH-INDUCING ABILITY OF ADIPOSE STEM CELLS COMPRISING UDENAFIL AS ACTIVE INGREDIENT

CROSS-REFERENCE TO RELATED APPLICATIONS

The present application claims priority to Korean Patent Application No. 10-2018-0062118 filed on May 30, 2018, the disclosure of which is incorporated herein by reference in its entirety.

BACKGROUND OF THE INVENTION

1. Field of the Invention

The present invention was supported by a grant from the National Research Foundation (NRF-2016R1D1A1B03932050) and was also supported by the National Research Foundation (NRF-2017R1A6A3A11035599) funded by the Korean government.

The present invention relates to a hair growth-inducing ability enhancing effect of adipose stem cells obtained by performing treatment with udenafil and performing culture, and to a hair growth-inducing ability enhancing effect caused by IL-4 and IL-12B whose expression levels are increased in the adipose stem cells. In addition, the present invention provides a composition for preventing or treating alopecia, or promoting hair growth, comprising, as an active ingredient, adipose stem cells obtained by performing treatment with udenafil and performing culture.

2. Description of the Related Art

Human hair is primarily responsible for a defense function to protect the scalp from external stimuli such as ultraviolet rays and are also responsible for an aesthetic function to express the individual's external image. However, in modern society, hair loss is frequently caused by natural factors such as environmental pollution and strong ultraviolet rays, or physiological factors such as stress and hormonal imbalance. Unlike the past when a phenomenon of hair loss limitedly occurred in adult males, the phenomenon of hair loss currently occurs regardless of sex and age. Therefore, materials for prevention and treatment of hair loss are urgently needed.

The hair follicle, a physiological organ in the body that produces hair, is involved in the process ranging from hair growth to maintenance and exfoliation, and allows hair to grow and to be maintained as a hair growth cycle repeats. Recently, interest in activity of the hair follicle has increased as a phenomenon of hair loss has increased and demand for promotion of hair growth has increased in recent years.

Currently, representative drugs approved by the FDA as drugs that can promote hair growth are minoxidil and finasteride. However, these drugs are accompanied by side effects such as hair growth of the whole body and deterioration of sexual function. In addition, for such drugs, a specific mechanism of action is not clearly elucidated. Therefore, efforts have been made to develop a drug which is stable in the human body while promoting proliferation of dermal papilla cells in the hair follicle and increasing expression of growth factors.

As a candidate group that can serve as such a stable drug, adipose stem cells may be presented. Adipose stem cells are mesenchymal stem cells that exhibit effects of healing skin wound and preventing aging. According to what has been reported, it has been identified that adipose stem cells, which are in a hypoxic state or have been preconditioned with vitamin C, cause a hair growth cycle of mouse to be changed from a dormant phase to a growth phase, and thus can induce a hair-regenerating ability (Won, Chong Hyun, et al. "Hair growth promoting effects of adipose tissue-derived stem cells." Journal of dermatological science 57.2 (2010): 134-137; and Kim, Ji Hye, et al. "The molecular mechanism underlying the proliferating and preconditioning effect of vitamin C on adipose-derived stem cells." Stem cells and development 23.12 (2014): 1364-1376). In addition, it has been reported that regulation of activity of adipose stem cells can cause the adipose stem cells to have a further increased hair growth-inducing ability (KR 10-1686229 B1).

SUMMARY OF THE INVENTION

Accordingly, the present inventors have made efforts to develop a method for causing adipose stem cells, which exhibit a hair growth-promoting effect, to have a further enhanced hair growth-inducing ability. As a result, the present inventors have identified that in a case where adipose stem cells are treated with udenafil and cultured, IL-4 and IL-12B expression levels are increased in the adipose stem cells, so that the adipose stem cells induce maturation of hair follicle cells and allow the hair follicle cells to exhibit a further increased hair growth-inducing ability. In addition, the present inventors have identified that IL-4 and IL-12B, on their own, also induce maturation of the hair follicle cells and allow the hair follicle cells to exhibit an increased hair growth-inducing ability. Thus, the present inventors have completed the present invention.

An object of the present invention is to provide a method capable of further enhancing a hair growth-inducing ability exhibited by adipose stem cells.

Another object of the present invention is to provide a composition for preventing or treating alopecia, or promoting hair growth, comprising adipose stem cells having a further increased hair growth-inducing ability.

Yet another object of the present invention is to provide a composition for preventing or treating alopecia, or promoting hair growth, comprising factors whose expression levels are increased in adipose stem cells having a further increased hair growth-inducing ability, that is, IL-4 and IL-12B.

Still yet another object of the present invention is to provide a method for proliferating adipose stem cells, comprising culturing adipose stem cells in a medium supplemented with udenafil or a pharmaceutically acceptable salt thereof.

Still yet another object of the present invention is to provide a method for preventing or treating alopecia, or promoting hair growth, comprising administering, to an individual, adipose stem cells which have been treated with udenafil or a pharmaceutically acceptable salt thereof, or a culture thereof.

Still yet another object of the present invention is to provide a method for preventing or treating alopecia, or promoting hair growth, comprising administering, to an individual, a cytokine whose expression level is increased in adipose stem cells obtained by performing treatment with udenafil or a pharmaceutically acceptable salt thereof and performing culture.

In order to achieve the above objects, the present invention provides a composition for enhancing a hair growth-inducing ability of adipose stem cells, comprising, as an active ingredient, udenafil or a pharmaceutically acceptable salt thereof.

In addition, the present invention provides a method for proliferating adipose stem cells, comprising culturing adipose stem cells in a medium supplemented with udenafil or a pharmaceutically acceptable salt thereof.

In a preferred embodiment of the present invention, the udenafil may have a structure represented by the following Formula 1:

[Formula 1]

In a preferred embodiment of the present invention, the udenafil may induce increased IL-4 and IL-12B expression levels in adipose stem cells.

In a preferred embodiment of the present invention, adipose stem cells may be allowed to be treated with the udenafil which is at a concentration of 0.1 μM to 1 mM.

In addition, the present invention provides a pharmaceutical composition for preventing or treating alopecia, or promoting hair growth, comprising, as an active ingredient, adipose stem cells obtained by performing treatment with udenafil or a pharmaceutically acceptable salt thereof and performing culture, or a culture thereof.

In addition, the present invention provides a method for preventing or treating alopecia, or promoting hair growth, comprising administering, to an individual, adipose stem cells which have been treated with udenafil or a pharmaceutically acceptable salt thereof, or a culture thereof.

In addition, the present invention provides a cosmetic composition for preventing or ameliorating alopecia, or promoting hair growth, comprising, as an active ingredient, adipose stem cells obtained by performing treatment with udenafil or a pharmaceutically acceptable salt thereof and performing culture, or a culture thereof.

In addition, the present invention provides a pharmaceutical composition for preventing or treating alopecia, or promoting hair growth, comprising, as an active ingredient, a cytokine whose expression level is increased in adipose stem cells obtained by performing treatment with udenafil or a pharmaceutically acceptable salt thereof and performing culture.

In addition, the present invention provides a method for preventing or treating alopecia, or promoting hair growth, comprising administering, to an individual, a cytokine whose expression level is increased in adipose stem cells obtained by performing treatment with udenafil or a pharmaceutically acceptable salt thereof and performing culture.

In addition, the present invention provides a cosmetic composition for preventing or ameliorating alopecia, or promoting hair growth, comprising, as an active ingredient, a cytokine whose expression level is increased in adipose stem cells obtained by performing treatment with udenafil or a pharmaceutically acceptable salt thereof and performing culture.

In a preferred embodiment of the present invention, the cytokine may be any one or more selected from the group consisting of IL-4 and IL-12B.

The present invention provides a composition for enhancing a hair growth-inducing ability of adipose stem cells, comprising udenafil as an active ingredient. In a case where a culture medium of adipose stem cells is treated with udenafil and cultured, IL-4 and IL-12B expression levels are increased in the adipose stem cells, and thus maturation of hair follicle cells is further promoted, so that hair growth can be induced. Such a hair growth-inducing ability is exhibited at a remarkably increased level as compared with a hair growth-inducing ability exhibited by adipose stem cells obtained by performing culture without treatment with udenafil. Thus, the adipose stem cells obtained by performing treatment with udenafil and performing culture can be used as an active ingredient of a composition for preventing or ameliorating alopecia, or promoting hair growth. In addition, in a case where IL-4 and IL-12B, which are expressed in the adipose stem cells obtained by performing treatment with udenafil and performing culture, are applied to skin tissue, hair growth can be induced. Thus, IL-4 and IL-12B can be used as an active ingredient of a composition for preventing or ameliorating alopecia, or promoting hair growth.

DETAILED DESCRIPTION OF THE INVENTION

Hereinafter, terms used in the present invention will be described.

As used herein, the term "hair loss" means a phenomenon in which hair completely falls out of the scalp. A person who is undergoing hair loss has a hair cycle with a shorter growth phase and a longer dormant phase. Adipose stem cells obtained by performing treatment with udenafil and performing culture in accordance with the present invention have an increased ability to induce maturation of hair follicle cells, and thus induce hair growth, thereby exhibiting an improved effect on hair loss.

As used herein, the term "hair growth" means that hair grows in the scalp, and specifically means causing hair follicles to be formed in an area where hair loss has occurred or an area having no hair (hairless area) and inducing hairiness. This is used synonymously with "hair nutrue" or "hair cultivation" which means that a length of hair is increased in the art (that is, upgrowth of hair).

Hereinafter, the present invention will be described in detail.

The present invention provides a composition for enhancing a hair growth-inducing ability of adipose stem cells, comprising udenafil as an active ingredient.

In addition, the present invention provides a method for proliferating adipose stem cells, comprising culturing adipose stem cells in a medium supplemented with udenafil or a pharmaceutically acceptable salt thereof.

The udenafil according to the present invention is a PDE5 inhibitor which, in a case of being introduced into smooth muscle through the corpus cavernosal artery, suppresses activity of the PDE5 enzyme and prevents inactivation of intracellular cGMP so that activity of cGMP is maintained for a long time. In this manner, the udenafil can promote an erectile response to sexual stimuli, and thus has been conventionally used as a therapeutic agent for erectile dysfunction. More specifically, it is preferable that the udenafil has a structure represented by the following Formula 1.

[Formula 1]

In a case where a culture of adipose stem cells is treated with the udenafil and cultured, stimulation of the adipose stem cells can be induced, and thus IL-4 and IL-12B expression levels in the adipose stem cells can be increased. Specifically, the adipose stem cells are preferably treated with the udenafil which is at a concentration of 0.1 μM to 1 mM, but the concentration of the udenafil is not limited thereto. The udenafil may be adjusted to an appropriate concentration by a person skilled in the art and added to the culture of adipose stem cells.

The composition according to the present invention may comprise a pharmaceutically acceptable salt of the udenafil. In a case where the udenafil is used in the form of a pharmaceutically acceptable salt, an acid addition salt thereof formed by a pharmaceutically acceptable free acid is useful. The acid addition salt is obtained from inorganic acids such as hydrochloric acid, nitric acid, phosphoric acid, sulfuric acid, hydrobromic acid, hydroiodic acid, nitrous acid, and phosphorous acid, and non-toxic organic acids such as aliphatic mono- and dicarboxylates, phenyl-substituted alkanoates, hydroxyalkanoates and alkanedioates, aromatic acids, and aliphatic and aromatic sulfonic acids. Such pharmaceutically non-toxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluene sulfonate, chlorobenzene sulfonate, xylene sulfonate, phenyl acetate, phenylpropionate, phenylbutyrate, citrate, lactate, 3-hydroxybutyrate, glycolate, malate, tartrate, methanesulfonate, propanesulfonate, naphthalene-1-sulfonate, naphthalene-2-sulfonate, or mandelate.

The acid addition salt according to the present invention may be prepared by a conventional method, for example, by dissolving the udenafil in an excess amount of an acid aqueous solution, and causing this salt to be precipitated using a water-miscible organic solvent, for example, methanol, ethanol, acetone, or acetonitrile. The acid addition salt according to the present invention may be also prepared by heating equal amounts of udenafil and acid or alcohol in water, and then evaporating and drying the mixture, or performing suction filtration of the precipitated salt.

In addition, a base may be used to make a pharmaceutically acceptable metal salt of udenafil. An alkali metal or alkaline earth metal salt is obtained, for example, by dissolving the compound in an excess amount of an alkali metal hydroxide or alkaline earth metal hydroxide solution, filtering an undissolved compound salt, and evaporating and drying the filtrate. At this time, for the metal salt, it is pharmaceutically suitable to prepare a sodium, potassium, or calcium salt. In addition, a silver salt corresponding thereto is obtained by reacting an alkali metal or alkaline earth metal salt with a suitable silver salt (for example, silver nitrate).

In addition, the udenafil of the present invention includes not only pharmaceutically acceptable salts thereof, but also all salts, hydrates, and solvates thereof which can be prepared by conventional methods.

The addition salt according to the present invention may be prepared by a conventional method. For example, the addition salt may be prepared by dissolving udenafil in a water-miscible organic solvent, for example, acetone, methanol, ethanol, acetonitrile, or the like, adding an excess amount of an organic acid or an aqueous acid solution of an inorganic acid, and then performing precipitation or crystallization. Subsequently, the addition salt may be obtained by evaporating the solvent or an excess amount of the acid in this mixture, and then performing drying, or may be prepared by performing suction filtration of the precipitated salt.

In addition, the present invention provides a pharmaceutical composition for preventing or treating alopecia, or promoting hair growth, comprising, as an active ingredient, adipose stem cells obtained by performing treatment with udenafil or a pharmaceutically acceptable salt thereof and performing culture, or a culture thereof.

In addition, the present invention provides a method for preventing or treating alopecia, or promoting hair growth, comprising administering, to an individual, adipose stem cells which have been treated with udenafil or a pharmaceutically acceptable salt thereof, or a culture thereof.

In the present invention, the individual includes, but is not limited to, any one or more individuals selected from the group consisting of chickens, ducks, dogs, pigs, cows, horses, and humans. In addition, the individual may have hair loss or a hair loss disease.

In the present invention, the term "hair loss" or "hair loss disease" includes, but is not limited to, alopecia areata, androgenetic alopecia, telogen effluvium, traumatic alopecia, trichoti lomania, pressure alopecia, anagen effluvium, non-rigid alopecia, alopecia syphilitica, alopecia seborrheica, symptomatic alopecia, non-scarring alopecia, scarring alopecia, congenital alopecia, and the like, depending on types, symptoms, causes, or the like.

The udenafil and a pharmaceutically acceptable salt thereof have been described above with respect to the composition for enhancing a hair growth-inducing ability of adipose stem cells, and thus a repeated description will be omitted.

In a case where the composition of the present invention is used as a medical product, a pharmaceutical composition containing, as an active ingredient, adipose stem cells treated with udenafil or a pharmaceutically acceptable salt thereof may be prepared into, but not limited to, a variety of oral or parental dosage forms as follows and administered at the time of clinical administration.

Examples of formulations for oral administration include tablets, pills, light or soft capsules, liquids, suspensions, emulsions, syrups, granules, and elixirs. These formulations contain, in addition to the active ingredient, a diluent (for example, lactose, dextrose, sucrose, mannitol, sorbitol, cellulose, and/or glycine), and a lubricant (for example, silica, talc, stearic acid, and a magnesium or calcium salt thereof, and/or polyethylene glycol). The tablets may also contain a binder such as magnesium aluminum silicate, starch paste, gelatin, methylcellulose, sodium carboxymethylcellulose, and/or polyvinylpyrrolidine; and, in some cases, the tablets may contain a disintegrant such as starch, agar, alginic acid or a sodium salt thereof, or fizzy water, and/or an absorbent, a colorant, a flavoring agent, and a sweetening agent.

The pharmaceutical composition comprising, as an active ingredient, adipose stem cells treated with the udenafil of the present invention or a pharmaceutically acceptable salt thereof may be administered parenterally, and the parenteral administration is performed by intravenous injection, subcutaneous injection, muscular injection, intraperitoneal injection, transdermal administration, or the like. At this time, the route of administration is preferably determined depending on a type of disease to which the pharmaceutical composition is applied. For example, since the pharmaceutical composition of the present invention is used for promotion of hair growth, or prevention and treatment of alopecia, administration thereof is preferably performed in such a way that the pharmaceutical composition is applied topically to the skin. Therefore, the pharmaceutical composition for promoting hair growth according to the present invention is preferably an injection for topical administration, but is not limited thereto. In order to make a formulation for parental administration, the adipose stem cells may be mixed with a stabilizer or buffer in water to prepare a solution or suspension, and the solution or suspension may be prepared into an ampoule or vial unit dosage form. The composition may be sterilized and/or may contain adjuvants such as a preservative, a stabilizer, a hydrating agent or an emulsifying promoter, a salt and/or a buffer for regulating osmotic pressure, and other therapeutically useful substances; and the composition may be made into preparations according to a conventional method which is a mixing, granulation, or coating method.

The pharmaceutical composition of the present invention can provide a desired effect of preventing or treating alopecia, or promoting hair growth in a case of containing an effective amount of adipose stem cells or a culture thereof. In the present invention, the term "effective amount" means an amount of the composition which exhibits an effect of preventing or treating alopecia, or promoting hair growth. The effective amount of the adipose stem cells or a culture thereof to be contained in the composition of the present invention will vary depending on the form in which the composition is commercialized, the method by which the compound is applied to the skin, and the time during which the compound stays on the skin. For example, in a case where the composition is commercialized as a medical product for preventing or treating alopecia, the composition may contain the adipose stem cells or a culture thereof at a higher concentration than a case of being commercialized as a cosmetic product which is routinely applied to the skin.

In addition, the present invention provides a cosmetic composition for preventing or ameliorating alopecia, or promoting hair growth, comprising, as an active ingredient, adipose stem cells obtained by performing treatment with udenafil or a pharmaceutically acceptable salt thereof and performing culture, or a culture thereof.

In addition, the adipose stem cells which have been treated with udenafil or a pharmaceutically acceptable salt thereof, or a culture thereof, as provided in the present invention, may be provided as a quasi-drug for preventing or ameliorating alopecia, or promoting hair growth.

The udenafil and a pharmaceutically acceptable salt thereof have been described above with respect to the composition for enhancing a hair growth-inducing ability of adipose stem cells, and thus a repeated description will be omitted.

The cosmetic composition of the present invention contains, as an active ingredient, adipose stem cells which have been treated with udenafil or a pharmaceutically acceptable salt thereof, or a culture thereof, and may be prepared, together with a dermatologically acceptable excipient, in the form of a basic cosmetic composition (lotion, cream, essence, facial cleanser such as cleansing foam and cleansing water, pack, body oil), a color cosmetic composition (foundation, lipstick, mascara, makeup base), a composition for hair products (shampoo, rinse, hair conditioner, hair gel), soap, and the like. In addition, the cosmetic composition of the present invention may be provided as an appropriate formulation of cosmetic composition, for example, in the form of a suspension, a microemulsion, a microcapsule, a microgranule, or an ionic (liposomal) or non-ionic follicular dispersion, and in the form of an ointment, an essence, a spray, or a conceal stick. In addition, the cosmetic composition of the present invention may also be prepared in the form of a foam or an aerosol composition which further contains a compressed propellant.

The excipient may include, but is not limited to, for example, a skin emollient, a skin penetration enhancer, a colorant, a perfume, an emulsifier, a thickening agent, and a solvent. In addition, the cosmetic composition of the present invention may further contain a flavor, a pigment, a bactericide, an antioxidant, a preservative, a moisturizer, and the like, and may contain a viscosity-increasing agent, inorganic salts, a synthetic polymeric substance, and the like for the purpose of improving physical properties. For example, in a case where the cosmetic composition of the present invention is used to prepare a facial cleanser and soap, the facial cleanser and soap may be easily prepared by adding the adipose stem cells or a culture thereof to common facial cleanser and soap bases. In a case of preparing a cream, the cream may be prepared by adding the adipose stem cells to an ordinary oil-in-water (O/W) cream base. To the cream base can be further added a synthetic or natural material including a flavor, a chelating agent, a pigment, an antioxidant, a preservative, and the like; and a protein, a mineral, a vitamin, and the like for the purpose of improving physical properties.

An amount of the adipose stem cells or a culture thereof to be contained in the cosmetic composition of the present invention is preferably 0.001% to 10% by weight, and more preferably 0.01% to 5% by weight, with respect to a total weight of the entire composition. However, the amount is not limited thereto. In a case where the amount is less than 0.001% by weight, a desired effect of preventing or ameliorating alopecia, or promoting hair growth cannot be expected. In a case where the amount is more than 10% by weight, there may be difficulties in terms of safety or preparation of formulations.

In a case where the adipose stem cells of the present invention or a culture thereof is used as an active ingredient of a cosmetic composition or a quasi-drug composition, the adipose stem cells or the culture thereof exhibiting an effect of preventing or ameliorating alopecia, or promoting hair growth may be directly added or may be used together with another quasi-drug or quasi-drug ingredient; and the adipose stem cells or the culture thereof may be appropriately used according to a conventional method. A mixing amount of the active ingredients can be suitably determined depending on a purpose of use.

The quasi-drug for preventing or ameliorating alopecia, or promoting hair growth according to the present invention has no particular limitation in terms of formulations thereof, and may be variously formulated in the form of quasi-drugs known in the art to exhibit an effect of preventing or ameliorating alopecia, or promoting hair growth. The products thus formulated include sunscreen, suncream, sun lotion, sun spray, hair tonic, hair lotion, hair cream, hair spray, hair mousse, hair gel, hair conditioner, hair shampoo, hair rinse, hair pack, hair treatment, eyebrow-growing solution, eyelash-growing solution, eyelash nourisher, pet shampoo, pet rinse, hand cleaner, detergent soap, soap, disinfectant cleaner, wet tissue, mask, ointment, patch, filter filler, and the like, and encompass all quasi-drugs in a common sense.

In addition, the present invention provides a pharmaceutical composition for preventing or treating alopecia, or promoting hair growth, comprising, as an active ingredient, a cytokine whose expression level is increased in adipose stem cells obtained by performing treatment with udenafil or a pharmaceutically acceptable salt thereof and performing culture.

In addition, the present invention provides a method for preventing or treating alopecia, or promoting hair growth, comprising administering, to an individual, a cytokine whose expression level is increased in adipose stem cells obtained by performing treatment with udenafil or a pharmaceutically acceptable salt thereof and performing culture.

In addition, the present invention provides a cosmetic composition for preventing or ameliorating alopecia, or promoting hair growth, comprising, as an active ingredient, a cytokine whose expression level is increased in adipose stem cells obtained by performing treatment with udenafil or a pharmaceutically acceptable salt thereof and performing culture.

The udenafil and a pharmaceutically acceptable salt thereof have been described above with respect to the composition for enhancing a hair growth-inducing ability of adipose stem cells, and thus a repeated description will be omitted.

The pharmaceutical composition or cosmetic composition of the present invention has been described above with respect to the composition comprising the adipose stem cells obtained by performing treatment with udenafil or a pharmaceutically acceptable salt thereof and performing culture, or a culture thereof, and thus a repeated description will be omitted.

In the pharmaceutical composition or cosmetic composition of the present invention, the cytokine means a cytokine whose mRNA or peptide (protein) expression level is increased in adipose stem cells obtained by performing culture in a culture medium treated with udenafil. Specifically, the cytokine is more preferably, but is not limited to, IL-4, IL-12B, or both.

EXAMPLES

Hereinafter, the present invention will be described in more detail by way of examples. It will be apparent to those skilled in the art that these examples are only for illustrating the present invention and that the scope of the present invention should not be interpreted as being limited by these examples.

Example 1

Identification of Hair Growth-Promoting Effect Caused by Udenafil

It was identified whether adipose stem cells stimulated by udenafil can exhibit a hair growth-inducing effect.

<1-1> Identification of Hair Growth-Inducing Effect Caused by Udenafil-Stimulated Adipose Stem Cells First, adipose stem cells were preconditioned with udenafil to prepare stimulated adipose stem cells. Adipose stem cells were inoculated on a 100-nm dish and cultured. The following day, 1 µM udenafil was added to the culture medium and additional culture was performed for 3 to 4 days. Subsequently, adherent cultured adipose stem cells were detached with trypsin, and then obtained by centrifugation. The obtained adipose stem cells were prepared by being mixed with 100 µl of PBS.

Subsequently, the dorsal hair of 6-week-old C3H mice was completely removed, and the prepared adipose stem cells were injected thereinto at $1\times10^4$ cells each by subcutaneous injection. Hair growth was identified by observing the dorsum of the mice for 15 days after the injection. Then, the grown hair was obtained by shaving, weighed, and photographed.

Figure 1:
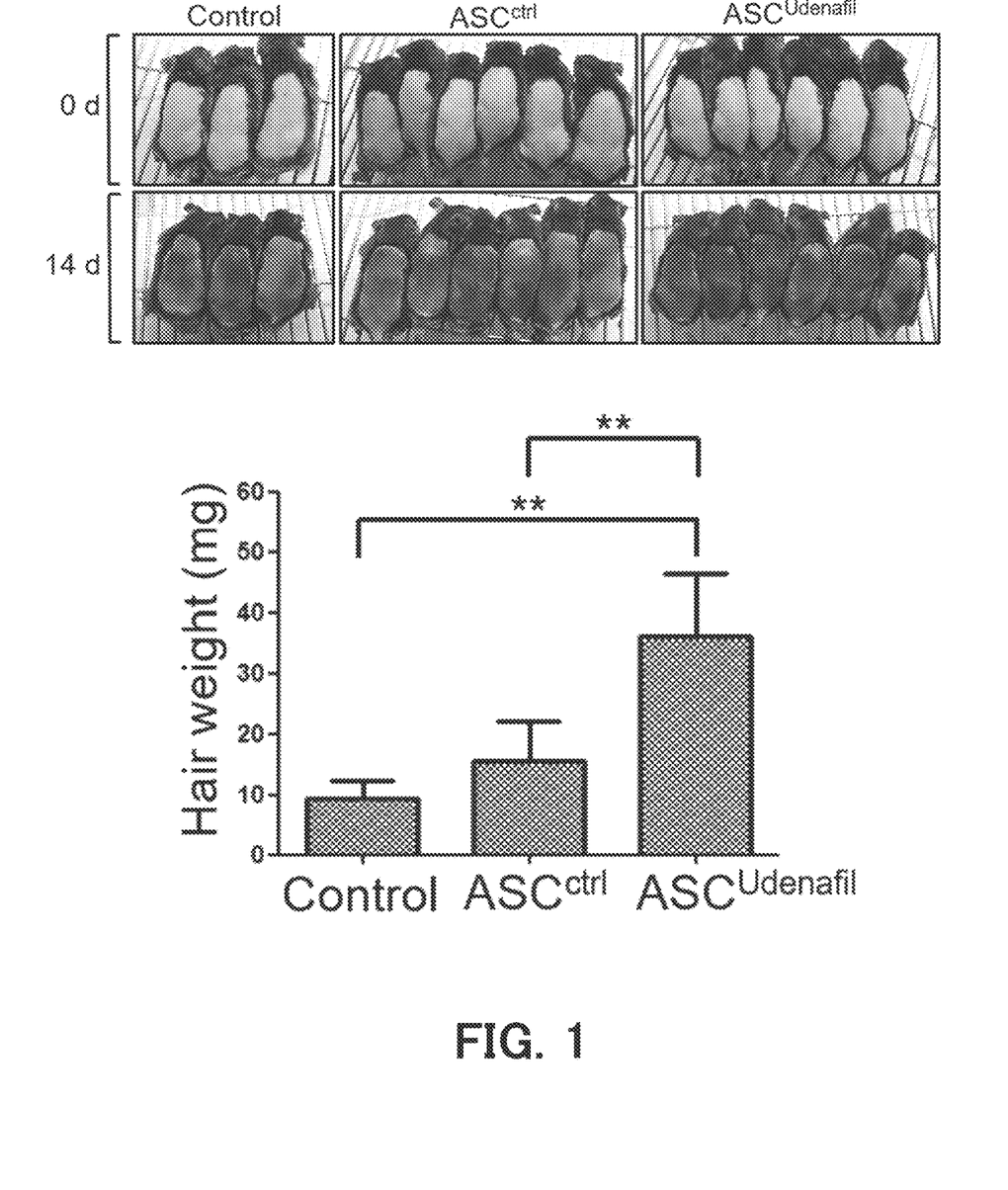
FIG. 1 illustrates results obtained by identifying a hair growth effect exhibited on the dorsum of mice into which adipose stem cells obtained by performing treatment with udenafil and performing culture have been subcutaneously injected.

As a result, as illustrated in FIG. 1, it was identified that a hair growth effect is exhibited in an experimental mouse group ($ASC^{Udenafil}$) into which udenafil-preconditioned adipose stem cells have been injected, and such a hair growth effect is significantly higher than that of an experimental mouse group ($ASC^{ctrl}$) into which non-preconditioned adipose stem cells have been injected.

<1-2> Observation of Tissue of Hair Follicle Cells Following Injection with Udenafil-Stimulated Adipose Stem Cells Tissue samples were produced to perform histological analysis. The dorsal skin of the mice for which observation had been completed in Example <1-1> was cut into squares of width×length=1 cm×1 cm, and then immersed in formalin at room temperature for 1 day to fix the tissues. The following day, the tissues were placed in a sample collection cassette and washed in running water for 15 minutes. Then, paraffin blocks were produced.

The produced paraffin blocks for the tissues were stained with H&E staining using the Mayer hematoxylin method, and the tissues were observed. The paraffin blocks were left to stand in a 65° C. incubator for about 10 minutes, to dissolve the paraffin. Then, the resulting products were immersed in three different xylenes for 10 minutes each. Then, the resulting products were washed by performing sequential immersion in 100%, 90%, 80%, and 70% ethanol for 1 minute each, and finally washed in water for about 3 minutes. Then, the resulting products were immersed in hematoxylin for about 9 minutes and washed in running water for 3 minutes. Again, the resulting products were immersed in eosin Y for 90 seconds and washed in running water for 3 minutes. Again, the resulting products were dehydrated by performing sequential immersion in 70%, 80%, 90%, and 100% ethanol for 2 minutes each, and immersed in xylene three times in total for 10 minutes each. Then, the resulting products were dried at room temperature and covered with cover glass to produce slides for observation. The produced slides for observation were observed with a microscope to identify tissues of stained hair follicle cells.

Figure 2:
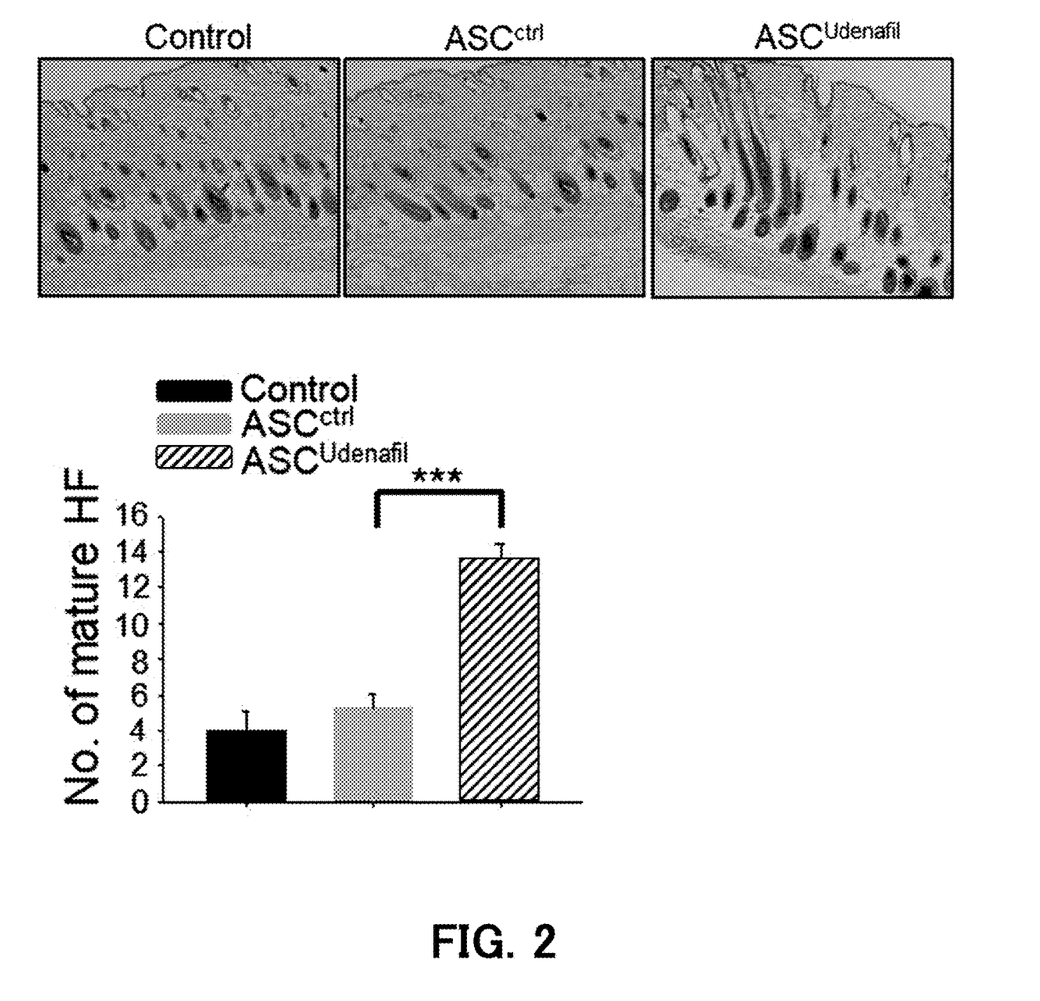
FIG. 2 illustrates results obtained by observing follicle tissue of the dorsum of mice into which adipose stem cells obtained by performing treatment with udenafil and performing culture have been subcutaneously injected.

As a result, as illustrated in FIG. 2, it was identified that the number of matured hair follicle cells is increased in the experimental group ($ASC^{Udenafil}$) into which udenafil-preconditioned adipose stem cells have been injected, as compared with the tissues of hair follicle cells in the control (Control) into which adipose stem cells have not been injected and the control ($ASC^{ctrl}$) into which adipose stem cells have been directly injected without preconditioning with udenafil.

Example 2

Identification of Adipose Stem Cell-Stimulating Effect Caused by Udenafil

<2-1> Identification of Change in Expression Level of Growth Factor Caused by Udenafil It was identified whether udenafil-treated adipose stem cells can exhibit a hair growth effect. In addition to this, in order to specifically identify whether the hair growth effect is caused by the udenafil-treated adipose stem cells, expression levels of IL-4 And IL-12B which are hair growth factors, were identified.

Specifically, as performed in Example <1-1>, adipose stem cells were treated with udenafil and cultured. After completion of the culture, the cells were obtained and RNA was extracted from the cells by treatment with TRIZOL™ (Invitrogen, NY, USA). Using the extracted RNA as a template, cDNA was synthesized through RT-PCR using oligodT and HELIXCRIPT™ Thermo Reverse Transcription System (NANOHELIX, WI, USA). The synthesized cDNA and BrightGreen qPCR master mix-ROX (abm, NY, US) were added to 96-well qPCR assay Kit for identifying growth factors [$RT^2$ First Strand (DNA Synthesis Kit (QIAGEN, MD, USA)], to perform a qPCR reaction. The results obtained by performing the qPCR reaction were analyzed using a program which corresponds to the $RT^2$ First Strand cDNA Synthesis Kit and is provided by QIAGEN, and IL-4 and IL-12B expression levels in the udenafil-treated adipose stem cells were respectively identified.

Figure 3:
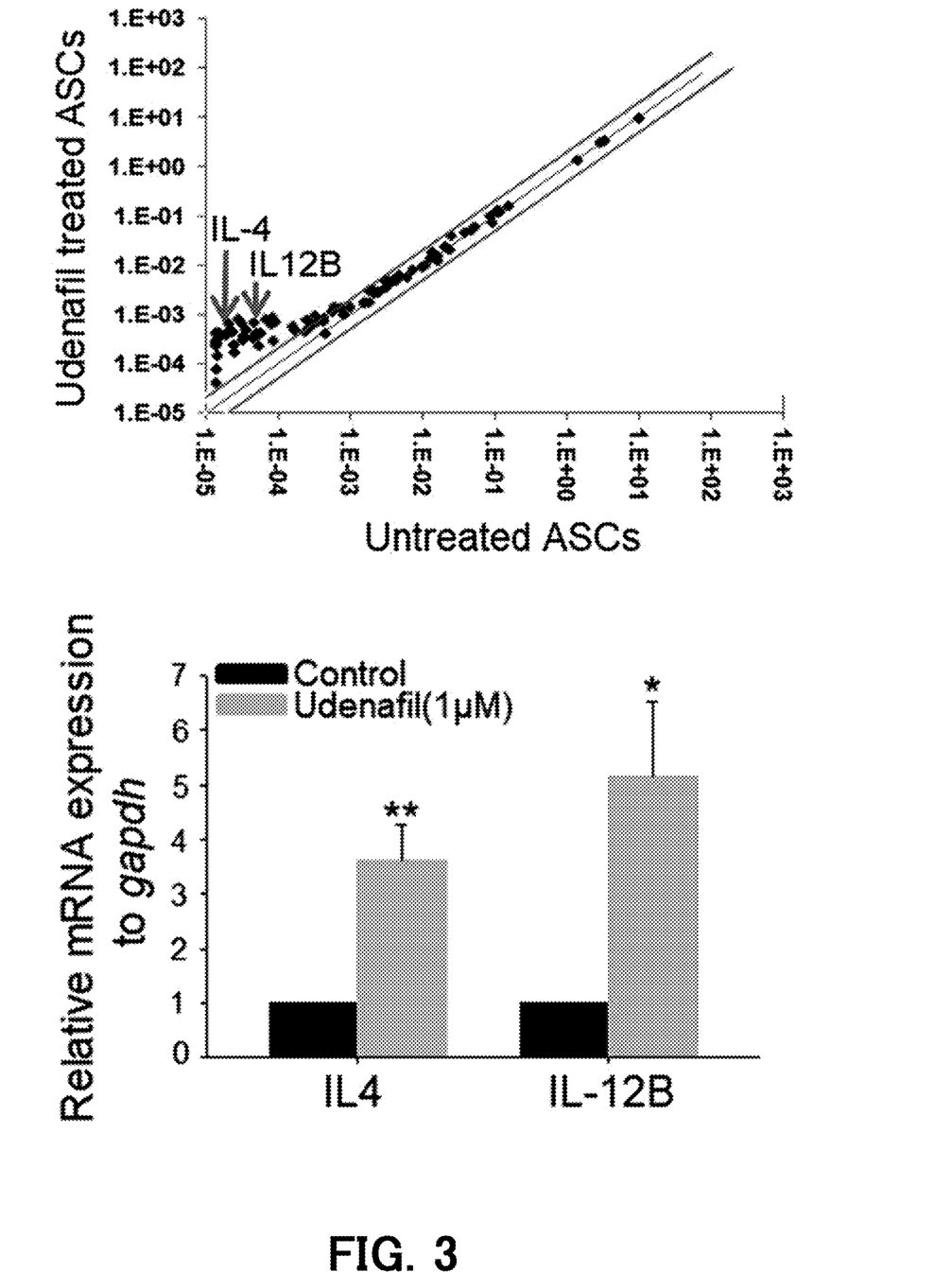
FIG. 3 illustrates results obtained by identifying mRNA expression levels of IL-4 and IL-12B expressed in adipose stem cells obtained by performing treatment with udenafil and performing culture.

As a result, as illustrated in FIG. 3, it was identified that the udenafil-treated adipose stem cells exhibit an about 4-fold higher IL-4 mRNA expression level and exhibits an about 6-fold higher IL-12B mRNA expression level, than the non-udenafil-treated adipose stem cells (Control).

<2-2> Identification of Hair Growth Effect of IL-4 and IL-12B

It was identified in Example <2-1> that the udenafil-treated adipose stem cells exhibit increased IL-4 and IL-12B expression levels. Thus, in addition to this, it was intended to identify a hair growth-inducing effect of IL-4 or IL-12B itself.

Specifically, the dorsal hair of 6-week-old C3H mice was completely removed, and 100 ng/ml of an IL-4 peptide or an IL-12B peptide was applied to the dorsum of the mice once a day. It was identified whether the hair was growing while applying the IL-4 peptide or IL-12B peptide for 13 to 14 days. Then, a photograph was taken and the dorsal skin tissue was obtained. The tissue was observed with H&E staining.

Figure 4:
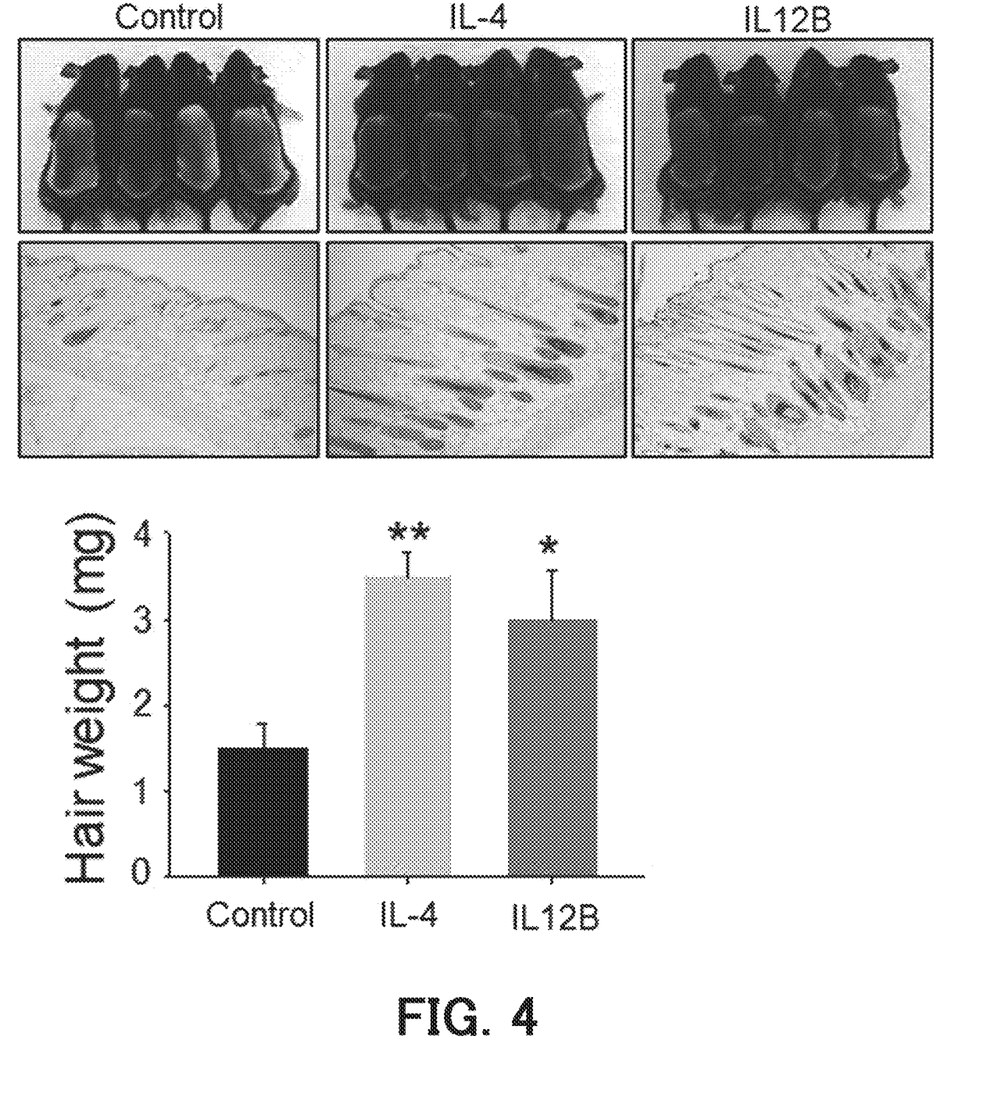
FIG. 4 illustrates results obtained by identifying a hair growth effect exhibited on the dorsum of mice to which an IL-4 peptide or an IL-12B peptide has been applied.

As a result, as illustrated in FIG. 4, it was identified that an increased hair growth effect is exhibited on the dorsum of the mice to which the IL-4 peptide or the IL-12B peptide has been applied, and the hair follicle tissue is also significantly maturated.

<2-3> Identification of Hair Growth-Inducing Effect of IL-4 and IL-12B

In addition, the vibrissal hair follicle of 5-week-old C57bl/6 mice was dissected to obtain hair follicle cells, and the hair follicle cells were transferred to 48-well plates. Then, treatment with 5 ng/ml or 20 ng/ml of an IL-4 peptide or an IL-12B peptide was performed and culture was performed for 3 days. After completion of the culture, the hair follicle tissue was photographed and a length of hair grown therefrom was measured.

Figure 5:
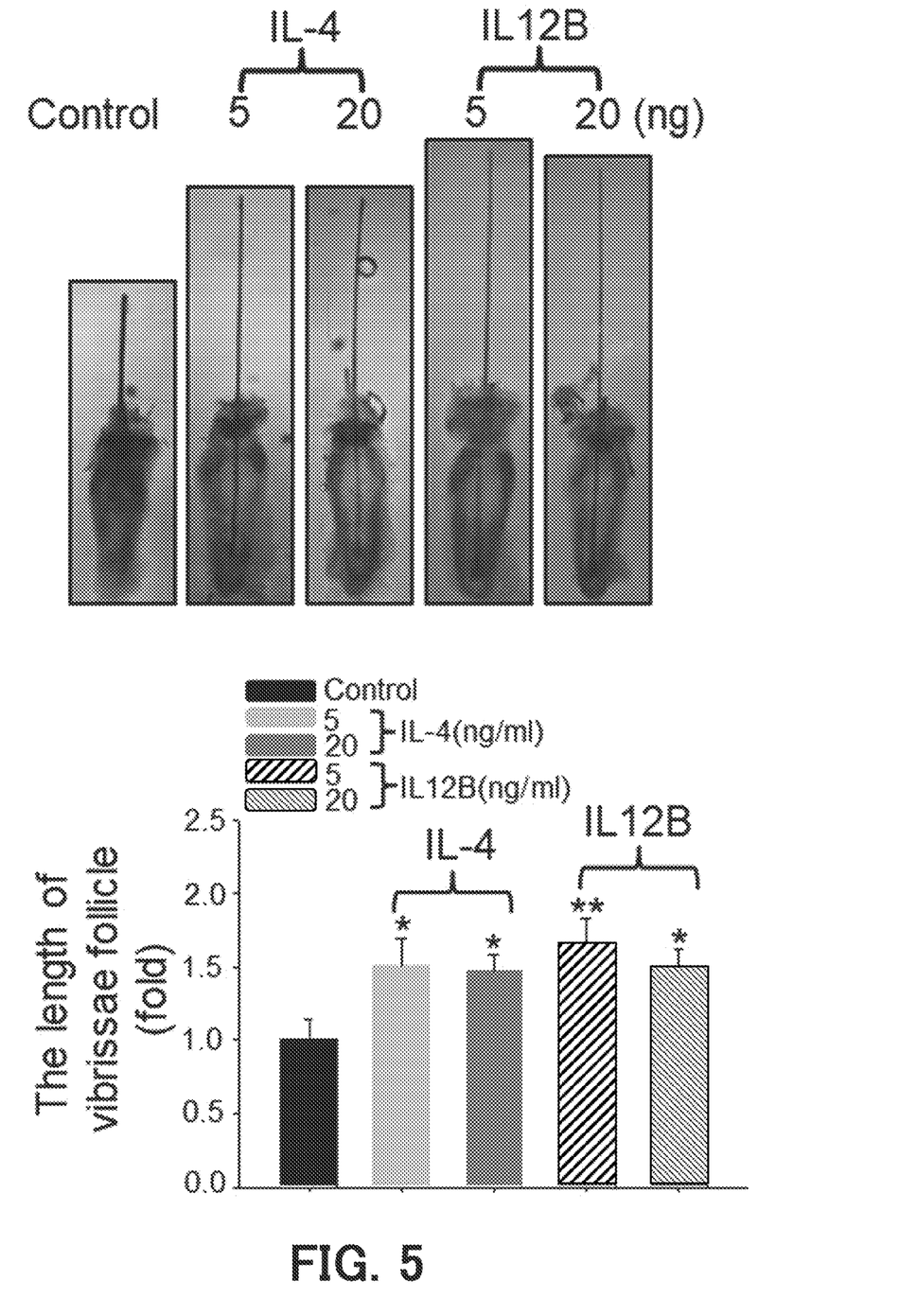
FIG. 5 illustrates results obtained by treating hair follicle cells obtained from the mouse nose with an IL-4 peptide or an IL-12B peptide and identifying a hair growth-inducing effect thereof.

As a result, as illustrated in FIG. 5, it was identified that in a case where the vibrissal hair follicle cells are cultured together with IL-4 or IL-12B, the length of hair grown from the hair follicle cells is longer than that of the non-treated control. From this, it was identified that IL-4 and IL-12B exhibit a hair growth-inducing effect.

Example 3

Effect of Udenafil on Proliferation and Migration of Adipose Stem Cells 3-1. Culture of Human Adipose Stem Cells Human adipose stem cells were isolated via liposuction of subcutaneous fat, as described in a previous study: Briefly, the fat was washed with phosphate-buffered saline (PBS), 0.075% collagenase was added, and the mixture was incubated for 45 minutes at 37° C. with gentle shaking. After centrifugation, the pellet was filtered through a 100 am nylon mesh. Then, the cells were cultured with an essential medium containing alpha Minimum Essential Medium (α-MEM) (Hyclone, Logan, Utah, USA), 10% fetal bovine serum (FBS) (Gibco, Carlsbad, Calif., USA), and 1% antibiotics (Gibco) for three passages. Then, the medium was changed to contain α-MEM, 10% FBS, and 1% penicillin/streptomycin (Gibco), and the cells were cultured for four passages. The adipose stem cells at passages 5 to 7 were used for all experiments. Characterization of the adipose stem cells was performed using flow cytometry. The adipose stem cells were positive for CD44, CD73, CD90, CD105, human leukocyte antigen (HLA)-I, and podocalyxin-like protein (PODXL), and were negative for hematopoietic markers such as CD34 and CD45. A multipotent differentiation potential was examined, as described in a previous study; as a result, the adipose stem cells could be differentiated into adipocytes, osteocytes, and chondrocytes. The adipose stem cells were maintained at 37° C. in a humidified 5% $CO_2$ incubator.

3-2. Cell Growth Assay

For cell growth assay, the adipose stem cells were seeded in 12-well plates, with $5\times10^3$ cells/well, treated with udenafil (0.1, 0.5, or 1 µM), and incubated for 7 days. The adipose stem cells were also seeded in 12-well plates, with $1\times10^4$ cells/well, treated with a synthetic peptide of IL-4 or IL-12B (100 ng/ml), and incubated for 7 days. The cells were then trypsinized, stained with trypan blue (Sigma-Aldrich, MO, USA), and counted each day using a hemocytometer.

3-3. Scratch Wound-Healing Assay

The adipose stem cells were seeded into 6-well plates and cultured to confluence. A sterile 1 ml pipette tip was used to scratch the cell monolayer. The cultures were then washed with PBS to remove de-plated cells, and the cells were again cultured with udenafil, or IL-4, and IL-12B in a serum-free medium for 3 days. Cell migration into the scratched area (wound closure) was visualized using a ZEISS™ Observer D1 microscope. Multiple images were acquired per well, and the average cell number within the wound was monitored over 3 days.

3-4. Transwell Migration Assay

The adipose stem cells were seeded into 60 mm plates and treated with udenafil IL-4, or IL-12B for 3 days. The adipose stem cells starved for 1 day ($1.5\times10^4$ cells/well) were suspended in a serum-free medium and seeded on the upper side of transwell membrane inserts (BD Falcon, CA, USA), which was pre-coated with MATRIGEL™ (1/60 dilution, BD MATRIGEL™ matrix, CA, USA). The normal serum With FBS was added in the lower side thereof as a chemoattractant. The cultures were incubated for 1 day to allow for transwell migration. The inserts were then removed, and the upper surface thereof was cleaned using a cotton swab and washed with PBS to remove non-migrating cells. The inserts were stained with 0.1% formalin/10% crystal-violet solution (Sigma-Aldrich) for 20 minutes, and the cell number was analyzed under a ZEISS™ Observer D1 microscope. Multiple images (15 to 20) were acquired per insert, and the average cell counts were calculated.

3-5. Tube Formation Assay Using MATRIGEL™

For this experiment, 12-well plates were coated with MATRIGEL™ (1/2 dilution, BD MATRIGEL™ matrix, CA, USA) and dried for 2 hours at 37° C. The adipose stem cells treated with endothelial cell basal medium-2 (EBM-2, LONZA, MD, USA) and udenafil were plated in MATRIGEL™-coated wells and incubated for 16 hours at 37° C. The number of tubes was analyzed under a ZEISS™ Observer D1 microscope.

3-6. Identification of Proliferation and Migration Effects of Adipose Stem Cells Caused by Treatment with Udenafil Although the adipose stem cells secrete various growth factors that promote hair growth, promotion of hair growth using preconditioning of adipose stem cells with trichogen is still unmet.

Figure 6:
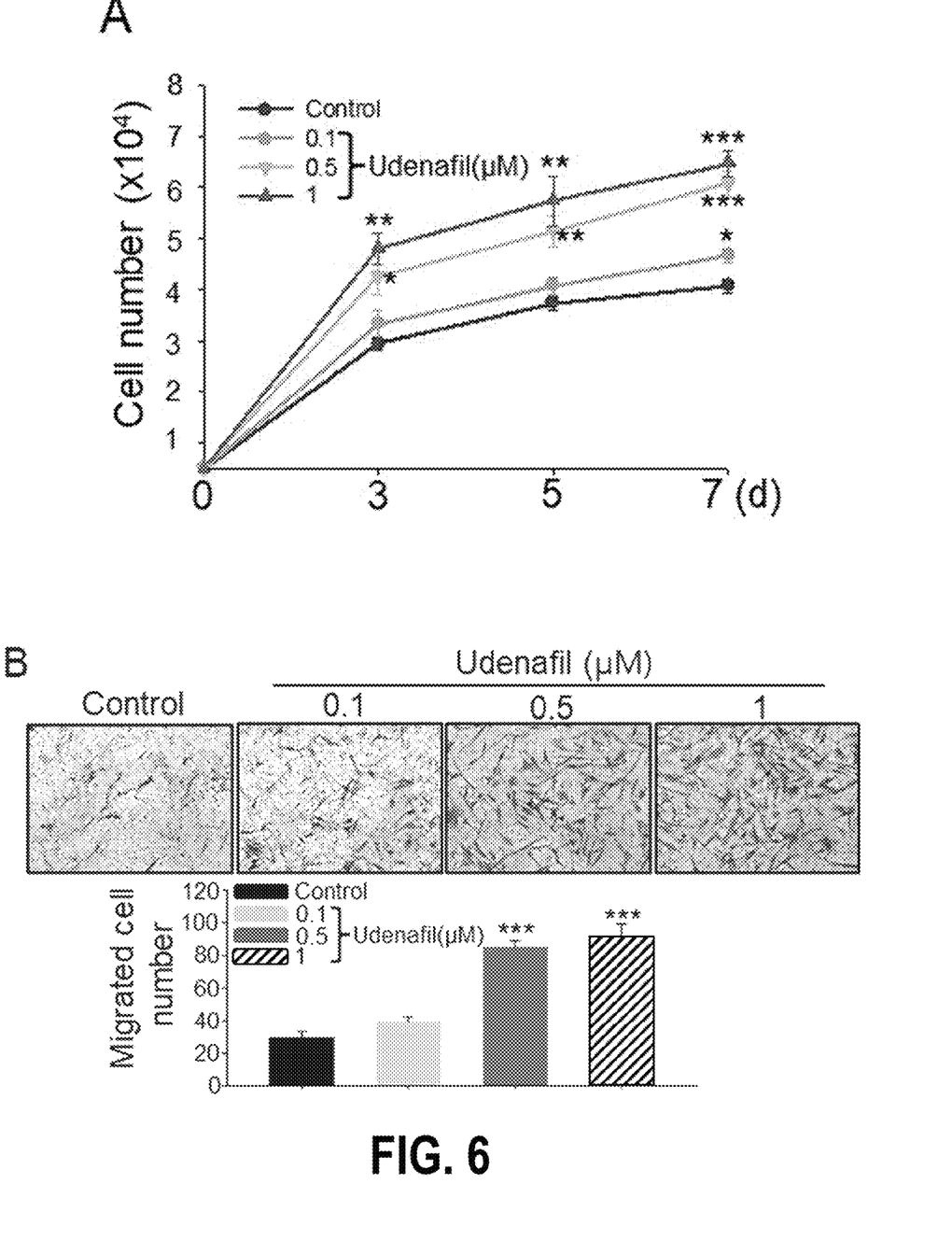
FIG. 6 illustrates results obtained by identifying increased proliferation and migration of adipose stem cells caused by treatment with udenhafil. A illustrates a result obtained by identifying the live cell number for 7 days after treatment with udenafil; B to D illustrate results obtained by identifying cell migration caused by treatment with udenafil; and E illustrates a result obtained by identifying tube formation caused by treatment with udenafil.

First, an effect of udenafil on growth and migration of human adipose stem cells was investigated. The live cell number was counted for 7 days after treatment with udenafil. It was found that udenafil increases growth of adipose stem cells in a time- and dose-dependent manner (FIG. 6(A)).

To investigate an effect of udenafil on ASC migration, transwell migration assay using insert and scratch wound-healing assay were conducted. The results showed that udenafil increases ASC migration in both assays in a dose-dependent manner (FIG. 6 (B to D)). Initially, it was believed that application of preconditioned udenafil to adipose stem cells stimulates vasodilatation and increases blood flow by inhibiting cGMP degradation (Gopal et al., 2001). Therefore, examination was conducted to see whether udenafil affects blood vessel formation in adipose stem cells. The result showed that udenafil increases the number of nascent tubes after 16 hours (FIG. 6(E)), indicating an increase in tube-forming activity of adipose stem cells. Collectively, these results suggested that udenafil may promote hair growth by enhancing proliferation and migration of adipose stem cells.

Example 4

Figure 7:
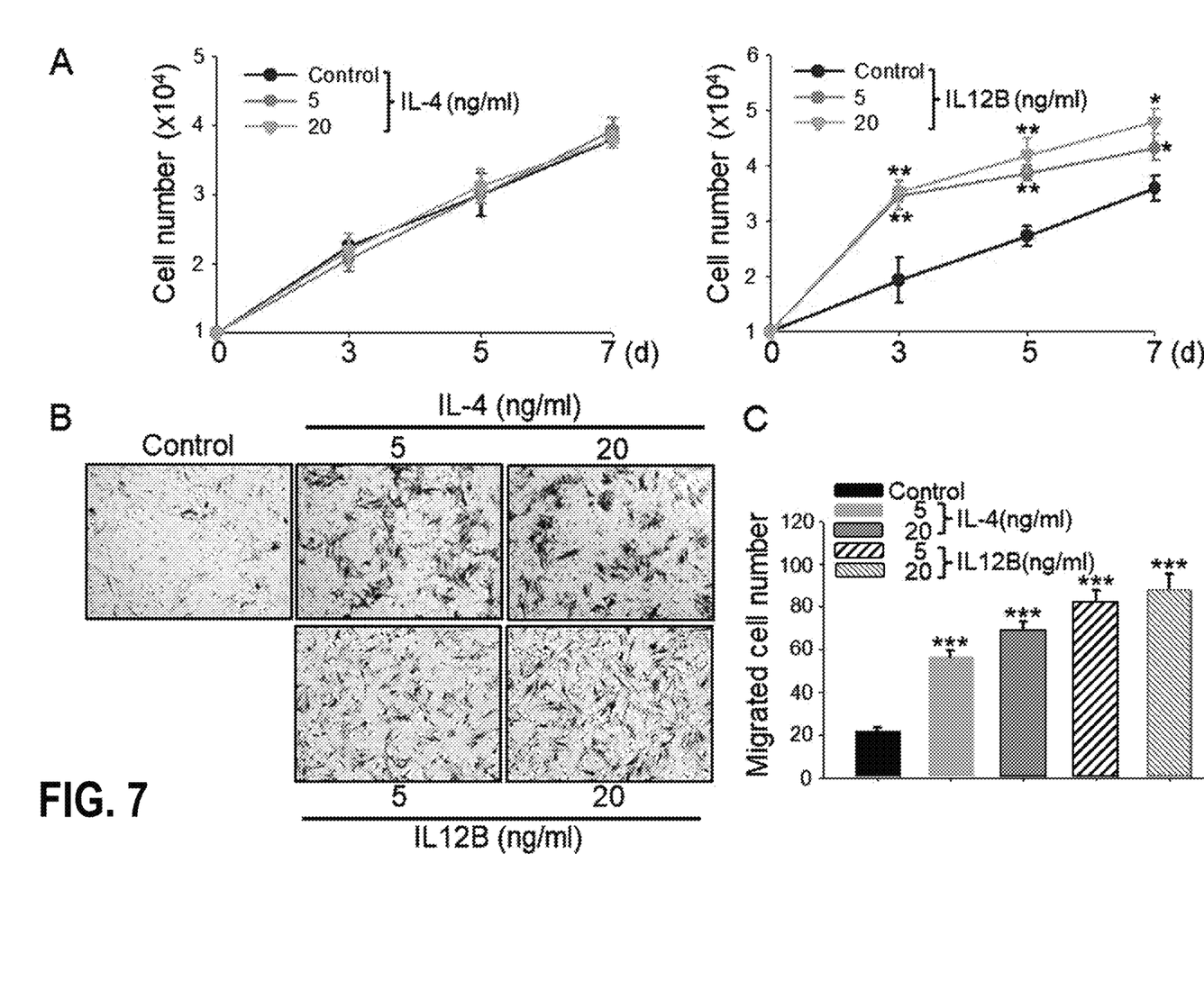
FIG. 7 illustrates results obtained by identifying proliferation and migration effects of adipose stem cells caused by treatment with IL-4 or IL-12B. A illustrates a result obtained by identifying the live cell number for 7 days after treatment with IL-4 or IL-12B; and B to E illustrate results obtained by identifying cell migration caused by treatment with IL-4 or IL-12B.

Identification of Effect of IL-4 and IL-12B on Proliferation and Migration of Adipose Stem Cells To examine whether IL-4 and IL-12B affect proliferation of adipose stem cells, the live cell number was followed for 7 days after treatment with IL-4 or IL-12B. It was found that IL-12B, not IL-4, increases proliferation of the adipose stem cells in a time- and dose-dependent manner (FIG. 7(A)).

Furthermore, to explore whether IL-4 and IL-12B affect migration of the adipose stem cells, transwell migration and scratch wound-healing assays were conducted. Both assays showed that IL-4 and IL-12B increase migration of the adipose stem cells in a dose-dependent manner (FIG. 7 (B to E)).

Figure 8:
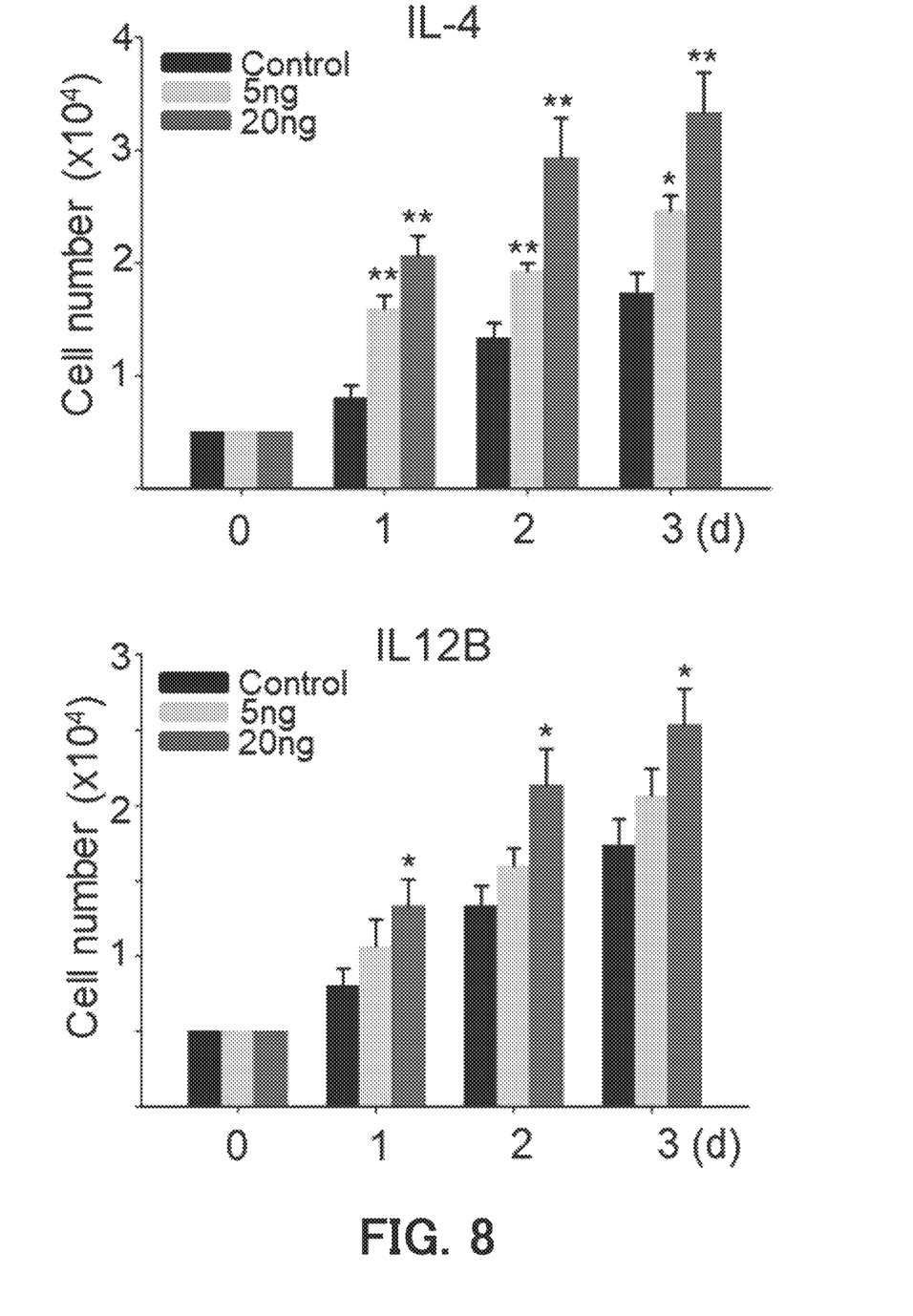
FIG. 8 illustrates results obtained by identifying proliferation effects of dermal papilla cells caused by treatment with IL-4 or IL-12B.

Collectively, these results suggested that IL-4 and IL-12B may promote hair growth by enhancing migration and partial proliferation of the adipose stem cells. To clarify how increased IL-4 and IL-12B in udenafil-treated adipose stem cells function in hair-compositing cells such as dermal papilla cells (DP cells), effects of IL-4 and IL-12B on the DP cells were examined. Indeed, treatment of each of IL-4 and IL-12B proteins increased growth of the DP cells (FIG. 8). This result suggested that IL-4 or IL-12B released from adipose stem cells increases growth of DP cells, thereby stimulating hair growth.

What is claimed is:

1. A method for preventing or treating alopecia, or promoting hair growth in a subject in need thereof, comprising:
   administering to the subject adipose stem cells which have been treated with udenafil or a pharmaceutically acceptable salt thereof, or a culture of adipose stem cells which have been treated with udenafil or a pharmaceutically acceptable salt thereof,
   wherein the adipose stem cells treated with udenafil or a pharmaceutically acceptable salt thereof have increased IL-4 and IL-12B expression levels when compared with the same adipose stem cells not treated with udenafil.

2. The method according to claim 1, wherein the culture contains IL-4 and IL-12B.

3. The method according to claim 1, wherein the adipose stem cells are treated with udenafil and wherein the udenafil has a structure represented by the following Formula 1:

[Formula 1]

4. The method according to claim 1, wherein the adipose stem cells have been treated with the udenafil or a pharmaceutically acceptable salt thereof at a concentration of 0.1 µM to 1 mM.

5. The method of claim 1, wherein the method treats alopecia in the subject.

6. The method of claim 1, wherein the method prevents alopecia in the subject.

7. The method of claim 1, wherein the subject is a human who has been diagnosed with having alopecia.

* * * * *